US008481292B2

(12) United States Patent
Casbon et al.

(10) Patent No.: US 8,481,292 B2
(45) Date of Patent: Jul. 9, 2013

(54) INCREASING CONFIDENCE OF ALLELE CALLS WITH MOLECULAR COUNTING

(75) Inventors: James Casbon, Hinxton (GB); Sydney Brenner, Ely (GB); Robert Osborne, Great Chesterford (GB); Conrad Lichtenstein, Cambridge (GB); Andreas Claas, Saffron Walden (GB)

(73) Assignee: Population Genetics Technologies Litd., Cambridge (GB)

( * ) Notice: Subject to any disclaimer, the term of this patent is extended or adjusted under 35 U.S.C. 154(b) by 0 days.

(21) Appl. No.: 13/237,124

(22) Filed: Sep. 20, 2011

(65) Prior Publication Data
US 2012/0071331 A1    Mar. 22, 2012

Related U.S. Application Data

(60) Provisional application No. 61/385,001, filed on Sep. 21, 2010, provisional application No. 61/432,119, filed on Jan. 12, 2011.

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |
| C07H 21/00 | (2006.01) | |

(52) U.S. Cl.
USPC ......... 435/91.2; 435/6.1; 435/6.11; 435/6.12; 435/91.1; 536/23.1; 536/24.3; 536/24.33; 536/25.3

(58) Field of Classification Search
USPC ............. 435/6.1, 6, 11, 12, 91.1, 91.2, 91.51, 435/183; 436/94, 501; 536/23.1, 24.3, 24.33, 536/25.3
See application file for complete search history.

(56) References Cited

U.S. PATENT DOCUMENTS

| | | | |
|---|---|---|---|
| 6,440,706 | B1 | 8/2002 | Vogelstein et al. |
| 7,537,897 | B2 | 5/2009 | Brenner et al. |
| 7,824,889 | B2 | 11/2010 | Vogelstein et al. |
| 7,915,015 | B2 | 3/2011 | Vogelstein et al. |
| 8,168,385 | B2 | 5/2012 | Brenner |
| 2007/0020640 | A1 | 1/2007 | McCloskey et al. |
| 2009/0105959 | A1 | 4/2009 | Braverman et al. |
| 2010/0323348 | A1 | 12/2010 | Hamady et al. |

FOREIGN PATENT DOCUMENTS

| | | |
|---|---|---|
| WO | 2012129363 A2 | 9/2012 |
| WO | 2012142213 A2 | 10/2012 |

OTHER PUBLICATIONS

PCT/IB2011/003160, International Search Report and Written Opinion, dated May 7, 2012, 13pgs.
Grant, et al., "SNP genotyping on a genome-wide amplified DOP-PCR template", Nucleic Acids Res., 2002, 30:e125.

Makrigiorgos, et al., "A PCR-based amplification method retaining the quantitative difference between two complex genomes", Nat Biotechnol, 2002, 20:936-9.
Ogino, et al., "Quantification of PCR bias caused by a single nucleotide polymorphism in SMN gene dosage analysis", J Mol Diagn, 2002, 4:185-90.
Tomaz, et al., "Differential methylation as a cause of allele dropout at the imprinted GNAS locus", Genet Test Mol Biomarkers, 2010, 14:455-60.
Weber, et al., "A real-time polymerase chain reaction assay for quantification of allele ratios and correction of amplification bias", Anal Biochem, 2003, 320:252-8.
Wojdacz, et al., "Primer design versus PCR bias in methylation independent PCR amplifications", Epigenetics, 2009, 4:231-4.
Bonaldo, et al. Normalization and subtraction: two approaches to facilitate gene discovery. Genome Res. Sep. 1996;6(9):791-806.
Casbon, et al. A method for counting PCR template molecules with application to next-generation sequencing. Nucleic Acids Res. Jul. 2011;39(12):e81.
Cox. Bar coding objects with DNA. Analyst. May 2001;126(5):545-7.
Fu, et al. Counting individual DNA molecules by the stochastic attachment of diverse labels. Proc Natl Acad Sci U S A. May 31, 2011;108(22):9026-31.
Hensel, et al. Simultaneous identification of bacterial virulence genes by negative selection. Science. Jul. 21, 1995;269(5222):400-3.
Kinde, et al. Detection and quantification of rare mutations with massively parallel sequencing. Proc Natl Acad Sci U S A. Jun. 7, 2011;108(23):9530-5.
Kinde, et al. Supporting Information for Detection and quantification of rare mutations with massively parallel sequencing. Proc Natl Acad Sci U S A. Jun. 7, 2011;108(23):9530-5.
Kivioja, et al. Counting absolute numbers of molecules using unique molecular identifiers. Nat Methods. Nov. 20, 2011. doi: 10.1038/nmeth.1778. [Epub ahead of print].
McCloskey, et al. Encoding PCR products with batch-stamps and barcodes. Biochem Genet. Dec. 2007; 45 (11-12):761-7.
Miner, et al. Molecular barcodes detect redundancy and contamination in hairpin-bisulfite PCR. Nucleic Acids Res. Sep. 3, 2004;32(17):e135.

(Continued)

*Primary Examiner* — Frank Lu
(74) *Attorney, Agent, or Firm* — James S. Keddie; Bozicevic, Field & Francis, LLP

(57) ABSTRACT

Aspects of the present invention include methods and compositions for determining the number of individual polynucleotide molecules originating from the same genomic region of the same original sample that have been sequenced in a particular sequence analysis configuration or process. In these aspects of the invention, a degenerate base region (DBR) is attached to the starting polynucleotide molecules that are subsequently sequenced (e.g., after certain process steps are performed, e.g., amplification and/or enrichment). The number of different DBR sequences present in a sequencing run can be used to determine/estimate the number of different starting polynucleotides that have been sequenced. DBRs can be used to enhance numerous different nucleic acid sequence analysis applications, including allowing higher confidence allele call determinations in genotyping applications.

20 Claims, 3 Drawing Sheets

OTHER PUBLICATIONS

Qiu, et al. DNA sequence-based "bar codes" for tracking the origins of expressed sequence tags from a maize cDNA library constructed using multiple mRNA sources. Plant Physiol. Oct. 2003;133(2):475-81.

Shoemaker, et al. Quantitative phenotypic analysis of yeast deletion mutants using a highly parallel molecular bar-coding strategy. Nat Genet. Dec. 1996;14(4):450-6.

Yandell, et al. A probabilistic disease-gene finder for personal genomes. Genome Res. Sep. 2011;21(9):1529-42.

Zhang, et al. The impact of next-generation sequencing on genomics. J Genet Genomics. Mar. 20, 2011;38(3):95-109.

Shiroguchi, et al., "Digital RNA sequencing minimizes sequence-dependent bias and amplification noise with optimized single-molecule barcodes", Proc Natl Acad Sci, 2012, 109:1347-52.

Konig, et al., "iCLIP reveals the function of hnRNP particles in splicing at individual nucleotide resolution", Nat Struct Mol Biol, 2010, 17:909-15.

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: synthetic sequence

<400> SEQUENCE: 1
cctatcccct gtgtgccttg gcagtctcag ggacacccag ccaagacagc        50

<210> SEQ ID NO 2
<211> LENGTH: 380
<212> TYPE: DNA
<213> ORGANISM: Artificial Sequence
<220> FEATURE:
<223> OTHER INFORMATION: synthetic sequence

<400> SEQUENCE: 2
ccatctcatc cctgcgtgtc tccgactcag rybdhvbacr tagaatgtgc atggatcgta        60
tgagcacctg tgggcagggc aagtggcaga tgccttagtg gatctcactg gaagcctggc       120
agaaaggtgg agcttgaagg atgtaacgaa agccagcggc cagcaggaca gacccagtgg       180
tggggagcac agaacttgtc ggcagctact ccacctgaag gaccggtgtc taatcagctg       240
ctctgtgctt agcccagag caggtacagc tatggctaca actccctcca ccattagctt       300
gttacagaga aggaaatcgg tccttgagag gctgtcttgg ctgggtgtcc ctgagactgc       360
caaggcacac aggggatagg                                                  380

INCREASING CONFIDENCE OF ALLELE CALLS WITH MOLECULAR COUNTING

CROSS REFERENCE TO RELATED APPLICATION

This application claims priority from U.S. Provisional Application Ser. No. 61/385,001, filed on Sep. 21, 2010, and U.S. Provisional Application Ser. No. 61/432,119, filed on Jan. 12, 2011, both of which are incorporated herein by reference in their entirety.

BACKGROUND

Genotyping is an important technique in genetic research for mapping a genome and localizing genes that are linked to inherited characteristics (e.g., genetic diseases). The genotype of a subject generally includes determining alleles for one or more genomic locus based on sequencing data obtained from the subject's DNA. Diploid genomes (e.g., human genomes) may be classified as, for example, homozygous or heterozygous at a genomic locus depending on the number of different alleles they possess for that locus, where heterozygous individuals have two different alleles for a locus and homozygous individuals have two copies of the same allele for the locus. The proper genotyping of samples is crucial when studies are done in the large populations needed to relate genotype to phenotype with high statistical confidence.

In genotyping analysis of diploid genomes by sequencing, the coverage (number of sequencing reads) for a particular genomic locus is used to establish the confidence of an allele call. However, confidence in allele calling is significantly reduced when bias is introduced during sample preparation, e.g., when the starting sample is in limiting amounts and/or when one or more amplification reactions are employed to prepare the sample for sequencing. Thus, in samples having limited amounts of DNA, one may see high coverage (i.e., a high number of sequencing reads) for an allele on one chromosome over the allele on a different chromosome due to amplification bias (e.g., amplification from only a few, or even one, polynucleotide molecule). In this case, coverage alone may be misleading when measuring confidence in an allele call.

The present invention finds use in increasing the confidence in allele calling as well as in other applications based on nucleic acid sequence analysis, especially in the context of studying genotypes in a large population of samples.

SUMMARY OF THE INVENTION

Aspects of the present invention include methods and compositions for determining the number of individual polynucleotide molecules originating from the same genomic region of the same original sample that have been sequenced in a particular sequence analysis configuration or process. In these aspects of the invention, a degenerate base region (DBR) is attached to the starting polynucleotide molecules that are subsequently sequenced (e.g., after certain process steps are performed, e.g., amplification and/or enrichment). The number of different DBR sequences present in a sequencing run can be used to determine/estimate the number of individual polynucleotide molecules originating from the same genomic region of the same original sample that have been sequenced in a particular sequence analysis configuration or process. DBRs can be used to improve the analysis of many different nucleic acid sequencing applications. For example, DBRs enable the determination of a statistical value for an allele call in genotyping assays that cannot be derived from the read number alone.

In certain embodiments, aspects of the subject invention are drawn to methods of determining the number of starting polynucleotide molecules sequenced from multiple different samples. In certain embodiments, the method includes: (1) attaching an adapter to starting polynucleotide molecules in multiple different samples, where the adapter for each sample includes: a unique MID specific for the sample; and a degenerate base region (DBR) (e.g., a DBR with at least one nucleotide base selected from: R, Y, S, W, K, M, B, D, H, V, N, and modified versions thereof); (2) pooling the multiple different adapter-attached samples to generate a pooled sample; (3) amplifying the adapter-attached polynucleotides in the pooled sample; (4) sequencing a plurality of the amplified adapter-attached polynucleotides, where the sequence of the MID, the DBR and at least a portion of the polynucleotide is obtained for each of the plurality of adapter-attached polynucleotides; and (5) determining the number of distinct DBR sequences present in the plurality of sequenced adapter-attached polynucleotides from each sample to determine or estimate the number of starting polynucleotides from each sample that were sequenced in the sequencing step.

BRIEF DESCRIPTION OF THE DRAWINGS

The invention is best understood from the following detailed description when read in conjunction with the accompanying drawings. Included in the drawings are the following figures.

DEFINITIONS

Figure 1:
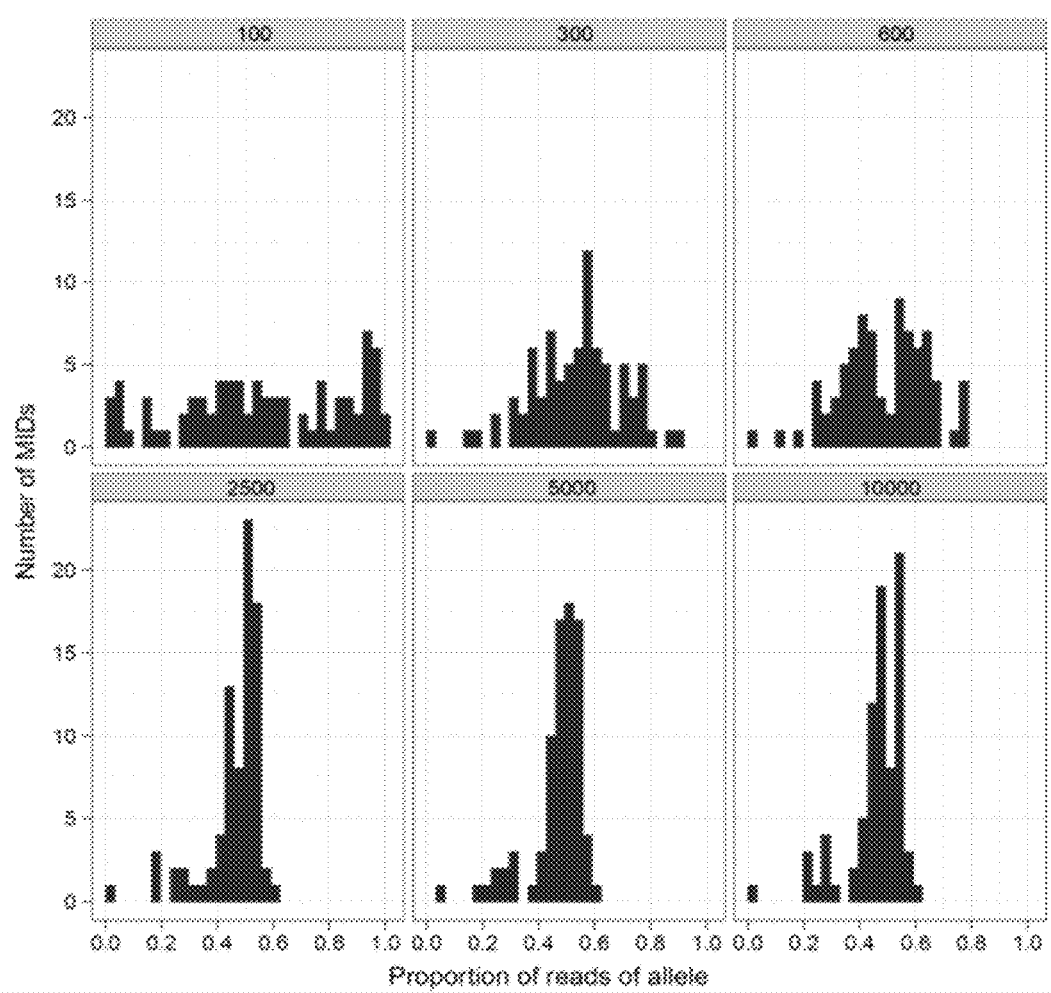
FIG. 1 shows the allele ratio for each MID in samples prepared from the indicated amount of starting material (top of each panel; in nanograms).

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "estimating", "assessing" and "assaying" are used interchangeably and includes quantitative and qualitative determinations. Assessing may be relative or absolute. "Assessing the presence of" includes determining the amount of something present, and/or determining whether it is present or absent.

Polynucleotides that are "asymmetrically tagged" have left and right adapter domains that are not identical. This process is referred to generically as attaching adapters asymmetrically or asymmetrically tagging a polynucleotide, e.g., a polynucleotide fragment. Production of polynucleotides having asymmetric adapter termini may be achieved in any convenient manner. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. Pat. No. 8,029,993, incorporated herein by reference in its entirety.

As one example, a user of the subject invention may use an asymmetric adapter to tag polynucleotides. An "asymmetric adapter" is one that, when ligated to both ends of a double stranded nucleic acid fragment, will lead to the production of primer extension or amplification products that have non-identical sequences flanking the genomic insert of interest. The ligation is usually followed by subsequent processing steps so as to generate the non-identical terminal adapter sequences. For example, replication of an asymmetric adapter attached fragment(s) results in polynucleotide products in which there is at least one nucleic acid sequence difference, or nucleotide/nucleoside modification, between the terminal adapter sequences. Attaching adapters asymmetrically to polynucleotides (e.g., polynucleotide fragments) results in polynucleotides that have one or more adapter sequences on one end (e.g., one or more region or domain, e.g., a primer binding site) that are either not present or have a different nucleic acid sequence as compared to the adapter sequence on the other end. It is noted that an adapter that is termed an "asymmetric adapter" is not necessarily itself structurally asymmetric, nor does the mere act of attaching an asymmetric adapter to a polynucleotide fragment render it immediately asymmetric. Rather, an asymmetric adapter-attached polynucleotide, which has an identical asymmetric adapter at each end, produces replication products (or isolated single stranded polynucleotides) that are asymmetric with respect to the adapter sequences on opposite ends (e.g., after at least one round of amplification/primer extension).

Any convenient asymmetric adapter, or process for attaching adapters asymmetrically, may be employed in practicing the present invention. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. Pat. No. 8,029,993, incorporated herein by reference in its entirety.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. A stable duplex can include Watson-Crick base pairing and/or non-Watson-Crick base pairing between the strands of the duplex (where base pairing means the forming hydrogen bonds). In certain embodiments, a non-Watson-Crick base pair includes a nucleoside analog, such as deoxyinosine, 2,6-diaminopurine, PNAs, LNA's and the like. In certain embodiments, a non-Watson-Crick base pair includes a "wobble base", such as deoxyinosine, 8-oxo-dA, 8-oxo-dG and the like, where by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand (wobble bases are described in further detail below). A "mismatch" in a duplex between two oligonucleotides or polynucleotides means that a pair of nucleotides in the duplex fails to undergo Watson-Crick bonding.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Multiplex Identifier" (MID) as used herein refers to a tag or combination of tags associated with a polynucleotide whose identity (e.g., the tag DNA sequence) can be used to differentiate polynucleotides in a sample. In certain embodiments, the MID on a polynucleotide is used to identify the source from which the polynucleotide is derived. For example, a nucleic acid sample may be a pool of polynucleotides derived from different sources, (e.g., polynucleotides derived from different individuals, different tissues or cells, or polynucleotides isolated at different times points), where the polynucleotides from each different source are tagged with a unique MID. As such, a MID provides a correlation between a polynucleotide and its source. In certain embodiments, MIDs are employed to uniquely tag each individual polynucleotide in a sample. Identification of the number of unique MIDs in a sample can provide a readout of how many individual polynucleotides are present in the sample (or from how many original polynucleotides a manipulated polynucleotide sample was derived; see, e.g., U.S. Pat. No. 7,537,897, issued on May 26, 2009, incorporated herein by reference in its entirety). MIDs are typically comprised of nucleotide bases and can range in length from 2 to 100 nucleotide bases or more and may include multiple subunits, where each different MID has a distinct identity and/or order of subunits. Exemplary nucleic acid tags that find use as MIDs are described in U.S. Pat. No. 7,544,473, issued on Jun. 6, 2009, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of MIDs employed to tag a plurality of samples need not have any particular common property (e.g., Tm, length, base composition, etc.), as the methods described herein can accommodate a wide variety of unique MID sets. It is emphasized here that MIDs need only be unique within a given experiment. Thus, the same MID may be used to tag a different sample being processed in a different experiment. In addition, in certain experiments, a user may use the same MID to tag a subset of different samples within the same experiment. For example, all samples derived from individuals having a specific phenotype may be tagged with the same MID, e.g., all samples derived from control (or wildtype) subjects can be tagged with a first MID while subjects having a disease condition can be tagged with a second MID (different than the first MID). As another example, it may be desirable to tag different samples derived from the same source with different MIDs (e.g., samples derived over time or derived from different sites within a tissue). Further, MIDs can be generated in a variety of different ways, e.g., by a combinatorial tagging approach in which one MID is attached by ligation and a second MID is attached by primer extension. Thus, MIDs can be designed and implemented in a variety of different ways to track polynucleotide fragments during processing and analysis, and thus no limitation in this regard is intended.

"Next-generation sequencing" (NGS) as used herein refers to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (Ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3): 333-43; and Zhang et al., "The impact of next-generation sequencing on genomics", J Genet Genomics, 2011, 38(3): 95-109.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few nanoliters, e.g. 2 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN™"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified.

"Polynucleotide" or "oligonucleotide" is used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. As described in detail below, by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand. Such monomers and their internucleosidic linkages may be naturally occurring or may be analogs thereof, e.g. naturally occurring or non-naturally occurring analogs. Non-naturally occurring analogs may include peptide nucleic acids (PNAs, e.g., as described in U.S. Pat. No. 5,539,082, incorporated herein by reference), locked nucleic acids (LNAs, e.g., as described in U.S. Pat. No. 6,670,461, incorporated herein by reference), phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Reflex site", "reflex sequence" and equivalents are used to indicate one or more sequences present in a polynucleotide that are employed to move a domain intra-molecularly from its initial location to a different location in the polynucleotide. The use of reflex sequences is described in detail in PCT application serial no. PCT/IB2010/02243 entitled "Compositions and Methods for Intramolecular Nucleic Acid Rearrangement", published on Feb. 24, 2011 as WO/2011/021102, and incorporated herein by reference. In certain embodiments, a reflex sequence is chosen so as to be distinct from other sequences in the polynucleotide (i.e., with little sequence homology to other sequences likely to be present in the polynucleotide, e.g., genomic or sub-genomic sequences to be processed). As such, a reflex sequence should be selected so as to not hybridize to any sequence except its complement under the conditions employed in the reflex processes. The reflex sequence may be a synthetic or artificially generated sequence (e.g., added to a polynucleotide in an adapter domain) or a sequence present normally in a polynucleotide being assayed (e.g., a sequence present within a region of interest in a polynucleotide being assayed). In the reflex system, a complement to the reflex sequence is present (e.g., inserted in an adapter domain) on the same strand of the polynucleotide as the reflex sequence (e.g., the same strand of a double-stranded polynucleotide or on the same single stranded polynucleotide), where the complement is placed in a particular location so as to facilitate an intramolecular binding and polymerization event on such particular strand. Reflex sequences employed in the reflex process described herein can thus have a wide range of lengths and sequences. Reflex sequences may range from 5 to 200 nucleotide bases in length.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, biotin-avidin or biotin-streptavidin interactions, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature (e.g., as measured in ° C.) at which a population of double-stranded nucleic acid molecules becomes half dissociated into single strands. Several equations for calculating the $T_m$ of nucleic acids are known in the art (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of $T_m$.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing nucleic acid molecule orientation and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, aspects of the present invention are drawn to the use of degenerate nucleotide bases (e.g., in a degenerate base region, or DBR) added to polynucleotides undergoing sequence analysis that find use in establishing the number of individual polynucleotide molecules originating from the same genomic region of the same original sample that have been sequenced in a particular sequence analysis configuration or process. Including a DBR in polynucleotides undergoing sequencing analysis finds use in a variety of genetic analyses, including increasing the confidence of allele calling by providing a mechanism to determine a statistical value for an allele call, a value that cannot be derived from the read number alone. The DBR may be added to a polynucleotide in any convenient manner, including as part of an adapter (or pool of adapters) attached to the polynucleotides being sequenced, e.g., the DBR can be in an adapter that also includes a sequencing primer site, or the DBR may be present in a nucleic acid synthesis primer, e.g., a PCR primer, such that the DBR is added to a target polynucleotide when the primer is used in a polymerization reaction.

DBRs also find use in performing genetic analyses on pooled polynucleotide samples in which each polynucleotide in the pooled sample includes a MID specific for its sample of origin (described in detail below). This allows a user to determine the sequence coverage of a specific polynucleotide species (or multiple species) from each of the samples of origin that were combined to generate the pooled sample. Thus, embodiments of the present invention include sequence analysis of polynucleotides in a pooled sample, where each polynucleotide contains a MID and a DBR.

Nucleic Acids

The present invention (as described in detail below) can be employed for the manipulation and analysis of nucleic acid sequences of interest (or polynucleotides) from virtually any nucleic acid source, including but not limited to genomic DNA, complementary DNA (cDNA), RNA (e.g., messenger RNA, ribosomal RNA, short interfering RNA, microRNA, etc.), plasmid DNA, mitochondrial DNA, synthetic DNA, etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the nucleic acids in the nucleic acid sample are derived from a mammal, where in certain embodiments the mammal is a human.

In certain embodiments, the nucleic acid sequences are enriched. By enriched is meant that the nucleic acids (e.g., in a polynucleotide sample) are subjected to a process that reduces the complexity of the nucleic acids, generally by increasing the relative concentration of particular nucleic acid species in the sample (e.g., having a specific locus of interest, including a specific nucleic acid sequence, lacking a locus or sequence, being within a specific size range, etc.). There are a wide variety of ways to enrich nucleic acids having a specific characteristic(s) or sequence, and as such any convenient method to accomplish this may be employed. The enrichment (or complexity reduction) can take place at any of a number of steps in the process, and will be determined by the desires of the user. For example, enrichment can take place in individual parental samples (e.g., untagged nucleic acids prior to adaptor ligation) or in multiplexed samples (e.g., nucleic acids tagged with adapter sequences encoding MID; MID are described in further detail below).

In certain embodiments, nucleic acids in the nucleic acid sample are amplified prior to analysis. In certain of these embodiments, the amplification reaction also serves to enrich a starting nucleic acid sample for a sequence or locus of interest. For example, a starting nucleic acid sample can be subjected to a polymerase chain reaction (PCR) that amplifies one or more region of interest. In certain embodiments, the amplification reaction is an exponential amplification reaction, whereas in certain other embodiments, the amplification reaction is a linear amplification reaction. Any convenient method for performing amplification reactions on a starting nucleic acid sample can be used in practicing the subject invention. In certain embodiments, the nucleic acid polymerase employed in the amplification reaction is a polymerase that has proofreading capability (e.g., phi29 DNA Polymerase, *Thermococcus litoralis* DNA polymerase, *Pyrococcus furiosus* DNA polymerase, etc.).

In certain embodiments, the nucleic acid sample being analyzed is derived from a single source (e.g., a single organism, virus, tissue, cell, subject, etc.), whereas in other embodiments, the nucleic acid sample is a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, 10,000 or more sources, 25,000 or more sources, etc.

In certain embodiments, nucleic acid fragments that are to be pooled with nucleic acid fragments derived from a plurality of sources (e.g., a plurality of organisms, tissues, cells, subjects, etc.), where by "plurality" is meant two or more. In such embodiments, the nucleic acids derived from each source include a multiplex identifier (MID) such that the source from which each tagged nucleic acid fragment was derived can be determined. In such embodiments, each nucleic acid sample source is correlated with a unique MID, where by unique MID is meant that each different MID employed can be differentiated from every other MID employed by virtue of at least one characteristic, e.g., the nucleic acid sequence of the MID. Any type of MID can be used, including but not limited to those described in co-pending U.S. patent application Ser. No. 11/656,746, filed on Jan. 22, 2007, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of MIDs employed to tag a plurality of samples need not have any particular common property (e.g., $T_m$, length, base composition, etc.), as the asymmetric tagging methods (and many tag readout methods, including but not limited to sequencing of the tag or measuring the length of the tag) can accommodate a wide variety of unique MID sets.

Degenerate Base Region (DBR)

Aspects of the present invention include methods and compositions for determining or estimating the number of individual polynucleotide molecules originating from the same genomic region of the same original sample that have been sequenced in a particular sequence analysis configuration or process. In these aspects of the invention, a degenerate base region (DBR) is attached to the starting polynucleotide molecules that are subsequently sequenced (e.g., after certain process steps are performed, e.g., amplification and/or enrichment, e.g., PCR). As detailed below, evaluating the number (and in some cases, the combination) of different DBR sequences present in a sequencing run allows the establishment of the number (or minimum number) of different starting polynucleotides that have been sequenced for a particular polynucleotide (or region of interest; ROI). This number can be used, for example, to give a statistical measure of confidence in allele calls, thus increasing the confidence in making such allele determinations (e.g., when calling homozygous alleles). DBRs also allow for the identification of potential sequencing or amplification errors that negatively impact genetic analysis if undetected.

DNA sequencing typically includes a step of attaching an adapter to the polynucleotides in a sample to be sequenced, where the adaptor contains a sequencing primer site (e.g., by ligation). As used herein, a "sequencing primer site" is a region of a polynucleotide that is either identical to or complementary to the sequence of a sequencing primer (when in a single stranded form) or a double stranded region formed between a sequencing primer sequence and its complement. The specific orientation of a sequencing primer site can be inferred by those of ordinary skill in the art from the structural features of the specific polynucleotide containing the sequencing primer site.

In addition to the sequencing primer site, a degenerate base region (DBR) is also attached to the polynucleotides, either as part of the adapter containing the sequencing primer site or independently (e.g., in a second adapter attached to the polynucleotide). Any convenient method for attaching or adding a DBR to the polynucleotides may be employed. A DBR is a region that can have a variable base composition or sequence (which may be considered as "random") as compared to other tagged polynucleotides in the sample. The number of different DBRs in a population of polynucleotides in a sample will be dependent on the number of bases in the DBR as well as the potential number of different bases that can be present at each position. Thus, a population of polynucleotides having attached DBRs with two base positions, where each position can be any one of A, C, G and T, will have potentially 16 different DBRs (AA, AC, AG, etc.). DBR may thus include 1, 2, 3, 4, 5, 6, 7, 8, 9, 10 or more bases, including 15 or more, 20 or more, etc. In certain embodiments the DBR is from 3 to 10 bases in length. Moreover, each position in a DBR may have a different base composition. For example, a 4 base DBR may have any of the following compositions: NNNN; NRSN; SWSW; BDHV (see Table 1 below for IUPAC nucleotide code). It is further noted that in certain embodiments, a base in a DBR may vary by virtue of having a detectable modification or other moiety attached thereto. For example, certain next generation sequencing platforms (e.g., Pacific Biosciences™) can be used to detect methylation differences in bases during the sequencing process. As such, a non-methylated base in a DBR could be distinguished from a methylated base in a DBR. No limitation with regard to the length or base composition of a DBR is therefore intended.

| IUPAC nucleotide code | Base |
| --- | --- |
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |

-continued

| IUPAC nucleotide code | Base |
| --- | --- |
| V | A or C or G |
| N | any base |

It is noted here that a DBR may be a single region (i.e., having all nucleotide bases adjacent to one another) or may be present in different locations on a polynucleotide (i.e., the bases of the DBR are separated by non-DBR sequences, also called a split DBR). For example, a DBR may have one or more bases in a first adapter at a first location on a polynucleotide and one or more bases in a second adapter at a second location on the same polynucleotide (e.g., the DBR may have bases present at both ends of an asymmetrically tagged polynucleotide, i.e., a polynucleotide having asymmetric adapters). No limitation in this regard is intended.

DBRs may be designed to facilitate detecting errors that occur in DBRs during amplification processes that are carried out prior to sequence analysis and/or errors that occur in the sequencing reaction itself. In such embodiments, the DBR sequences employed are designed such that an error in a DBR sequence does not necessarily lead to the generation of another possible DBR sequence (thereby resulting in incorrectly identifying replicons derived from the same template as being from a different template due to a DBR mutation). Consider, for example, the use of a DBR with sequence N. An error in the N would turn one DBR into another, which might lead us to overestimate the probability that we were correctly assigning a genotype. Compare this to a DBR with sequence Y. If we see an R at this position we know that there has been an error. While the correct DBR cannot necessarily be assigned to this error-containing DBR, we can detect that it is due to an error (e.g., in sequencing or amplification).

In some embodiments, degenerate base sequences may be used as combined MIDs-DBRs that can both (1) assign sample identify and (2) trace/count molecules. Consider, for example, two samples, one tagged with YYY and the other tagged with RRR. In our sequencing reaction we observe a MID-DBR with the sequence TAT, which fits neither of the combined MID-DBR sequence structure. One mutation is required to convert YYY to TAT. Two mutations are required to convert RRR to TAT. Therefore we would be able to say that there is a higher probability that the MID-DBR was YYY rather than RRR.

Description of exemplary error identifying (or error correcting) sequences can be found throughout the literature (e.g., in are described in US patent application publications US2010/0323348, entitled "Method and compositions for using error-detecting and/or error-correcting barcodes in nucleic acid amplification process", and US2009/0105959 entitled "System and method for identification of individual samples from a multiplex mixture", both incorporated herein by reference).

In certain embodiments in which the DBR is present within an adapter population that includes other functional domains (e.g., sequencing primer site, MID, reflex sequence), the functional domains in the adapter population will be identical to each other whereas the DBR will vary. In other words, unlike the other domains in an adapter population, the DBR has a variable (or random) base composition. By "adapter population", "population of adapters", and the like, is meant a sample of adapter molecules that are designed to be attached to the polynucleotides in a sample.

Generating adapters having a DBR may be achieved in any convenient manner, e.g., using DNA synthesis methods well known in the art (see citations in definitions section above).

Once attached to the polynucleotides in the parent sample, the polynucleotides may be subjected to further processing and ultimately sequenced. Processing steps that may be performed include any process steps that are desired by a user, e.g., enrichment, amplification, and the like. In the sequencing step, the sequence of the DBR as well as a portion of the polynucleotide (e.g., containing a region of interest) is obtained. Once the sequences are obtained, the number of different DBRs attached to a polynucleotide of interest is determined. This number can be employed to determine, or estimate, the number of different polynucleotides of interest from the starting parent sample that are represented in the sequencing results, where in some embodiments, the determined number is the minimum number of different polynucleotides of interest from the starting parent sample that are represented in the sequencing results.

Consider, for example, a two base DBR having base composition NN (where N is any deoxynucleotide base, i.e., A, G, C or T) employed in sequencing a locus to make an allele call for a particular subject sample (i.e., whether a subject is homozygous or heterozygous at the locus). Although there may be some biases from oligonucleotide synthesis, one can expect there to be 16 different DBRs in the population of adaptors with roughly equal probability (as described above). When a potential homozygous allele call is identified, determining the number of DBRs present in the sequencing run can be used to determine/estimate the number (or minimum number) of polynucleotide molecules that were actually sequenced (and thus the number that were amplified during the processing steps).

For diploid genomes, allele calling (in the ideal or theoretical case) can be modeled by the binomial distribution. Given that the two alleles copies (X and Y) differ at some site, the probability of observing all Xs or all Ys is given by the formula $(½)^c$, where c is the number of observations (reads) of the site. If we observe X ten times at a site (and no Y), we can say that the sample is likely to be homozygous for type X. The probability of an error in this call is therefore $(½)^{10}$ (just under one in a thousand).

Our experiments show that low amounts of DNA in the early stage of sample preparation can result in a high coverage of reads all corresponding to one allele, and that this can occur many more times than should be expected according to the binomial distribution. This is due to amplification of a few molecules of DNA (or even a single molecule) that results in a large number of reads derived from a genetic locus on a single chromosome (i.e., only one of the two diploid chromosomes actually present in the sample of interest). The result of this is that the error as a function of coverage deviates wildly from the predicted binomial error.

Using a DBR as described herein will increase the confidence in making allele calls from samples having limited amounts of DNA. For example, if 16 sequencing reads of one allele from a genetic locus all contain the DBR sequence GA, then it is likely that all these reads are from the same parent polynucleotide molecule (and thus a homozygous allele call is not justified). However, if the 16 sequencing reads each have a different DBR sequence, a homozygous call can be made with more confidence, as each read came from a different parent polynucleotide molecule.

It is noted here that in many embodiments, it is not possible to conclude that polynucleotides having identical DBR sequences are derived from the same parent polynucleotide molecule, as multiple identical DBRs may be present in the DBR-attached polynucleotides. For example, if an adapter population that contains a DBR of two N bases is used to tag a sample containing more that 16 polynucleotides, a subset of the tagged polynucleotides will have identical DBRs, and thus it will not be possible to determine that their sequences were derived from different parent polynucleotide molecules.

One exemplary way to determine more accurately the actual number of starting or parent molecules would be to increase the degeneracy of DBRs (i.e., to increase the number of unique sequences in the DBR used to label the particular sample of interest) so that every single molecule is likely to have a different DBR. In any event we can, in exemplary methods, either use the number of observed DBRs or else the probability distribution of the expected number of reads likely to produce the observed number of DBRs.

When calculating estimates of whether a particular allele call is a heterozygote or homozygote, one can create/employ an appropriate function $L(r,v)$ that returns the likelihood of a genotype given r reference and v variant reads. When employing DBRs as described herein, a modified function for calculating estimates $L(r', v')$ may be used, where r' is the number of unique DBRs for the reference read and v' is the number of unique DBRs for the variant read. Any convenient function for making allele calls may be employed and modified to employ data regarding DBR reads as described herein.

It is noted here that aspects of the invention can be used to increase the confidence in calling copy number variations in a polynucleotide sample, e.g., a genomic sample. Copy number variations can include genomic rearrangements such as deletions, duplications, inversions, and translocations or whole chromosome aneuploidies such as monosomies, disomies, trisomies, tetrasomies, and pentasomies. Consider, for example, a duplication event where parents have genotypes AC and CC at a given SNP, and the proband has genotype ACC. In the parent with genotype AC, given sufficient depth of sequencing coverage (i.e., sufficient sequencing reads), the number of DBRs associated with the C-allele and the A-allele are expected to be similar. In the proband, given sufficient depth of sequencing coverage, the number of DBRs associated with the C-allele is expected to be 2-times the number of DBRs associated with the A-allele, which provides evidence for duplication event encompassing the C-allele. The use of DBRs, rather than the number of sequencing reads, provides more confidence in calling a copy number variation since the DBR can be used to identify reads that derive from different polynucleotide molecules.

Exemplary Applications of DBRs

As detailed above, DBRs permit the statistical validation of sequence variants in a heterogeneous sample, including complex genomes or pools. For example, DBRs find use in the analysis of complex genomes in tumor samples, microbial samples, environmental samples, etc.

Below is provided exemplary statistical methods and exemplary applications of DBRs. The descriptions below are meant for exemplary purposes only and are not intended to limit the scope of employing DBRs in polynucleotide analyses.

Statistical Methods

As described above, in aspects of the present invention degenerate base runs (DBRs) are used to estimate, or get a quantitative measure of, the actual number of template molecules sequenced or analyzed in a given process. Two reads can have the same DBR either because the reads originate from the same template molecule or because the molecules received the same DBR by chance. The potential number of distinct template molecules sequenced ranges from the number of DBRs to the number of reads. The distribution of DBRs from a number of starting molecules is given by the occupancy distribution [see C. A. Charalambides and C. A. Charalambides. *Combinatorial methods in discrete distribu-*

*tions*. John Wiley and Sons, 2005]. Given an observed number of DBRs, the likely number of starting molecules can be calculated using maximum likelihood estimation, or other suitable techniques. Alternatively, for each DBR, the most likely template molecule can be estimated using the consensus sequence of all the reads with that particular DBR. The approaches can be combined to generate accurate estimates of the number of template molecules associated with particular variants.

DBRs in PCR Amplification

DBRs can be used to estimate or get a measure of the number of starting molecules used as templates for a PCR reaction. For example, a starting polynucleotide sample may be PCR-amplified for the first cycle, or first few cycles, using a PCR primer pair in which one (or both) primers include a generic primer sequence and a DBR 5' to the target specific sequence. After the initial cycle(s), this DBR-containing PCR primer pair may be removed or inactivated and replaced with PCR primers that do not have a DBR for the remaining cycles. The removal/inactivation of DBR-containing primers may be accomplished in any convenient manner, e.g., by physical or biochemical means. For example, DBR-containing primers may have attached thereto a first member of a binding pair (e.g., biotin), thereby facilitating removal of these primers by contacting the sample to the binding partner attached to a solid support (e.g., solid support-bound streptavidin) and collecting the non-bound fraction. Alternatively, free DBR-containing primers may be removed by treating the sample with a single-strand specific exonuclease (e.g., exonuclease I), by rendering the primers incapable of participating in further primer extension steps (e.g., by incorporating a dideoxynucleotide at the 3' end), or by a Solid Phase Reversible Immobilization (SPRI) process (e.g., Agencourt AMPure XP-PCR Purification, Beckman Coulter). The second PCR primers are designed to comprise sequences present on the 5' end of each of the first set of primers so as to replicate the DBR in templates generated from the DBR-containing PCR primers used in the first/first few cycles. Thus, the remaining cycles of PCR will amplify only the products of the first/first few cycles which contain DBRs. In another embodiment, the DBR-containing primers may be designed to have a higher Tm than the second set of primers not containing the DBR (i.e., the Tm of the target-specific sequence of the first PCR primers is higher than that of the second PCR primers specific for the 5' generic primer sequences). In this exemplary scenario, the DBR-containing primers may be present in limiting amounts and the first/first few cycles of the PCR be carried out at the higher Tm such that only the DBR-containing primers anneal and participate in nucleic acid synthesis. Because the DBR-containing primers are present in limiting amounts, they will be used up in the first/first few PCR cycles. Performing the remaining PCR cycles at a lower Tm will allow further amplification by the second set of PCR primers which do not include DBRs but that will replicate the DBRs from products of the first/first few cycles (as described above).

It is noted that there are many different combinations of PCR primers and amplification conditions that may be employed to accomplish the DBR PCR amplification described above. For example, such reactions may include 3 primers, where primer 1 (forward primer specific for the target polynucleotide and containing a DBR and 5' generic priming sequence) and primer 2 (reverse primer specific for the target polynucleotide and without a DBR) are used to amplify the target in the first/first few cycles, and primer 3 (forward primer specific for the 5' generic priming sequence of primer 1) and primer 2 are used for the remaining cycles.

It is further noted that tagging both ends of a PCR product with a DBR (i.e., where both primers used in the first/first few cycles include a DBR) may provide for increased confidence in estimating the number of starting polynucleotides amplified. It is noted that if greater than 2 cycles of PCR are used to attach DBRs, then it is necessary to take additional precautions during analysis of the data when using DBRs to trace the initial template (or starting) molecule from which products were amplified. This is due to the possibility that in the 3rd cycle of PCR, a PCR primer having a DBR can bind over an existing DBR site in a previously generated PCR product, thereby introducing a new DBR sequence. As outlined below, theoretical analysis of the first three cycles of PCR shows that it is possible to trace the lineage of a molecule. It is noted that the analysis below could theoretically be used for any number of PCR cycles for adding DBR sequences, although the depth of sequencing would have to be sufficient.

The method described below allows one to group sequence reads after >1 cycle of DBR addition using DBR-containing PCR primers. Table 1 shows each of the PCR products generated in each of three PCR cycles from a single double-stranded template (the template having top strand A and bottom strand B, as noted in Cycle 0 of FIG. 3). In Table I, each strand present in each cycle (denoted as letters A to P) are shown along with its respective template strand (i.e., the strand that served as the template during the synthesis of the indicated strand), and the 5' DBR and the 3' DBR present on the strand, if any (indicated as numbers 1 to 14). By "5' DBR" is meant a DBR sequence as it was incorporated as part of a PCR primer. By "3' DBR" is meant a complement sequence of a 5' DBR sequence (i.e., generated as a result of primer extension across an existing 5'DBR sequence). In cycle 3, one can see that DBR-overwriting may occur (indicated in the right-most column; see, e.g., strands K and N produced in cycle 3).

TABLE I

DBR Tagging in cycles 0 to 3 of a PCR reaction for a single double stranded template (A and B).

| Cycle | Strand | 5' DBR # | 3' DBR # | Template strand | DBR Overwriting |
|---|---|---|---|---|---|
| Cycle 0 | A | — | — | — | |
| | B | — | — | — | |
| Cycle 1 | A | — | — | — | |
| | B | — | — | — | |
| | C | 1 | — | A | |
| | D | 2 | — | B | |
| Cycle 2 | A | — | — | — | |
| | B | — | — | — | |
| | C | 1 | — | A | |
| | D | 2 | — | B | |
| | E | 3 | — | A | |
| | F | 4 | 1 | C | |
| | G | 5 | 2 | D | |
| | H | 6 | — | B | |
| Cycle 3 | A | — | — | — | |
| | B | — | — | — | |
| | C | 1 | — | A | |
| | D | 2 | — | B | |
| | E | 3 | — | A | |
| | F | 4 | 1 | C | |
| | G | 5 | 2 | D | |
| | H | 6 | — | B | |
| | I | 7 | — | A | |
| | J | 8 | 3 | E | |
| | K | 9 | 4 | F | overwriting of DBR 1 with DBR 9 |
| | L | 10 | 1 | C | |
| | M | 11 | 2 | D | |
| | N | 12 | 5 | G | overwriting of DBR |

TABLE I-continued

DBR Tagging in cycles 0 to 3 of a PCR reaction for a single double stranded template (A and B).

| Cycle | Strand | 5' DBR # | 3' DBR # | Template strand | DBR Overwriting |
|---|---|---|---|---|---|
| | O | 13 | 6 | H | 2 with DBR 12 |
| | P | 14 | — | B | |

Figure 3:
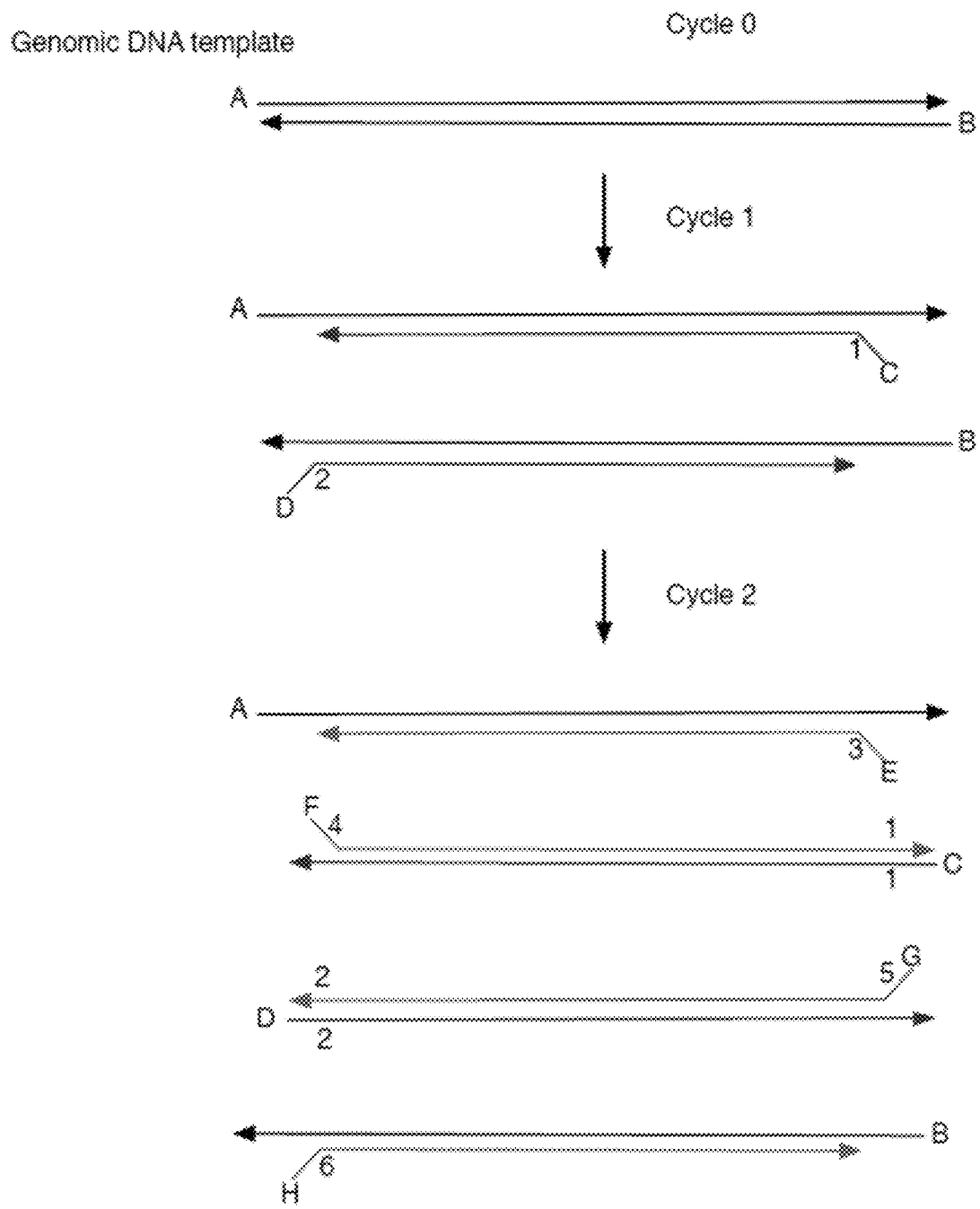
FIG. 3 shows the products produced in the first two cycles of PCR using primers having DBR sequences.

Table I above and FIG. 3 show the strands that have accumulated during the entire PCR process. (Note the carry-over of strands A and B from Cycle 0 to Cycles 1, 2, and 3; the carry-over of strands C and D in Cycle 1 to Cycles 2 and 3; etc.).

Given sufficient sequencing depth, DBRs can be used to trace back the originating molecule even if DBR over-writing has occurred. For example, strand K has 5' DBR #9 and 3' DBR #4. DBR #4 is shared with strand F, which has 5' DBR #4 and 3' DBR #1. DBR #1 is shared with strand C. Therefore strands K and F originally derive from strand C. Similarly, strand N has 5' DBR #12 and 3' DBR #5. DBR #5 is shared with strand G, which has 5' DBR #5 and 3' DBR #2. DBR #2 is shared with strand D. Therefore strands N and G originally derive from strand D.

As discussed above, DBR-containing PCR primers are removed after the first few cycles (e.g., after completion of Cycle 3 as shown in Table I).

FIG. 3 shows a schematic for the first 2 cycles of PCR for a single double stranded template as shown in Table I. At cycle 0, only the double-stranded template strands are present, i.e., top strand A and bottom strand B. Note that the direction of the arrows on each strand in FIG. 3 indicates the 5' to 3' direction. In the first PCR cycle (cycle 1), 2 products are produced by the PCR primer pair (both members of the primer pair including a DBR sequence), the first (C) having DBR #1 ("1" as shown in the figure) and the second (D) having DBR2 ("2" as shown in the figure). In the second cycle of PCR (cycle 2), the four templates (A, B, C and D) produce 4 products (E, F, G and H), each having a subsequent DBR attached (DBRs #3, #4, #5 and #6, respectively). Note that the products generated from templates C and D (F and G) now have DBRs at both ends. Cycle 3 (not shown in FIG. 3) then uses the 8 templates from cycle 2 to produce 8 products, each having additional DBRs attached (see products shown in Table I). Cycle 3 is the first cycle in which DBR over-overwriting can occur (i.e., priming and extension of templates F and G with subsequent DBR-labeled PCR primers will overwrite DBR #1 and DBR #2; these are shown in Table I as strands K and N).

In analyzing DBRs of polynucleotides in which DBR overwriting is possible, the reads are grouped according to the 5' and 3' DBR sequences and the lineage of the parental molecule is traced.

As is clear from the description above, the DBR is useful for (1) identification of PCR errors that arise during early cycles and (2) accuracy of allele calling/copy number determination. For error identification, it is clearly allowable to group independent priming events. The accuracy of allele calling calculations are slightly increased in complexity given that priming events do not necessarily represent independent starting molecules. However, it a reasonable assumption that priming events are equally likely on either allele, and thus this analysis is useful for improving the accuracy of allele calling.

For very low initial template copies using multiple cycles of DBR addition can be advantageous. For example, at very low DNA concentrations one might not recover a sufficient number of DBRs to give an accurate genotype using standard approaches. Allowing multiple priming events on the same template molecule can, in this case, give us sufficient confidence to make an allele call by providing more data.

Analysis of the DBRs in the final amplification products can be used to estimate the number of starting molecules amplified in the reaction. Such analysis will allow a user to determine if the products of the PCR reaction represent the selective amplification of only a few (or even one) starting polynucleotides and/or aid in the determination of PCR errors that have occurred during amplification (e.g., as described above).

DBRs in Heterogeneous Tumor Samples

DBRs also find use in assessing the heterogeneity of chromosomal abnormalities in tumor samples, e.g., within a single tumor or between different tumors in a subject. For example, one or more tumor samples can be obtained from a single tumor (e.g., at different locations within or around the tumor) and/or from different tumors in a subject and analyzed for genetic variation at one or more chromosomal locations. In certain embodiments, the samples may be obtained from a tumor (or subject) over time. Such variations can include specific base changes, deletions, insertions, inversions, duplications, etc., as are known in the art. DBRs may be employed to tag the polynucleotides in the tumor sample(s) prior to identifying the specific genetic variations, thereby providing a way to perform statistical analyses to validate any variants identified. For example, statistical analysis can be used to determine whether a detected variation represents a mutation in a subset of cells of the tumor, is a variation that is specific to a particular tumor in the subject, is a variation found in non-tumor cells in the individual, or is an artifact of the process by which the variant was identified (e.g., a PCR artifact).

DBRs in Assessing Microbial Diversity

DBR analysis can also be used in determining the genetic variation/diversity of a population of microbes/viruses in a single sample or between different samples (e.g., samples collected at different time points or from different locations). For example, samples collected form an individual over the course of an infection can be analyzed for genetic variation during the infection process using DBRs as described herein. However, no limitation on the type of microbial/viral sample is intended, and as such the sample can be from any source, e.g., from a subject with an infection, from an environmental source (soil, water, plants, animals or animal waste products, etc.), from a food source, or any other sample for which determination of the genetic diversity of the microorganisms in the sample, at one or more genetic locus or region, is desired. In practicing the methods, polynucleotides derived from the sample are labeled with DBRs as described herein (either before or after an enrichment step) and processed to identify genetic variations at one or more genetic site or locus of interest. Analysis of DBRs can then be performed to provide increased confidence in the determined genetic diversity of the microbes in the sample at the locus/loci of interest. Such analysis can be performed on samples collected from various sources and/or at various time points from a source. Exemplary genetic loci that find use in assessing microbial diversity include, but are not limited to, ribosomal RNA, e.g., 16S ribosomal RNA, antibiotic resistance genes, metabolic enzyme genes, etc.

DBRs in Assessing the Levels of Different Polynucleotide Species in a Sample

DBR analysis can also be used in assessing the levels of different polynucleotide species in a sample. Specifically, because DBR analysis can determine (or estimate) the number of parent polynucleotides in a sample, the relative or quantitative amount of specific polynucleotide species and the confidence in the determination of such species can be assessed. For example, analysis of a cDNA sample using DBRs can be employed to assess the relative or quantitative levels of different cDNA species in the sample, thus providing a way to determine their relative gene expression levels.

DBRs in Analyzing Pooled Samples

Another application of DBRs is in performing genetic analyses on pooled polynucleotide samples in which each polynucleotide in the pooled sample includes a MID specific for its sample of origin (described in detail above). This allows a user to determine the sequence coverage of a specific polynucleotide species (or multiple species) from each of the samples of origin that were combined to generate the pooled sample. This provides a mechanism to make sure that the polynucleotides from each starting sample in the pooled sample are represented adequately. Thus, embodiments of the present invention include sequence analysis of polynucleotides in a pooled sample, where each polynucleotide contains a MID and a DBR. It is noted that in these embodiments, the same DBR design may be used in conjunction with all parent samples/MIDs, as it is the combination of MID/DBR that is used in the sample-specific sequence analysis.

Pooled sample analyses using MIDs and DBRs finds us in numerous genetic analyses, including making allele calls, error correction of sequences, relative and quantitative gene expression analyses, and the like. It is noted that in analyzing polynucleotides in a pooled sample according to aspects of the present invention, it is important to maintain both the MID and DBR domains in each step of the workflow being employed, as loss of one or the other domain will negatively impact the confidence in the results obtained.

It is further noted that the use of MID and DBR domains in genetic analysis is especially powerful when combined with next-generation sequencing (NGS) platforms, many of which provide sequence data for each individual polynucleotide present in the sample to be sequenced. In contrast to conventional sequencing approaches in which individual clones of polynucleotides are sequenced independently, NGS platforms provide sequences for multiple different polynucleotides in a sample simultaneously. This difference allows for sample-specific statistical analyses to be done which are not constrained by having to clone and independently sequence each polynucleotide. Thus, the MID/DBR domain analyses described herein synergize with NGS platforms, providing improved statistical approaches to analyze the very large amounts of sequence data from pooled samples.

Kits and Systems

Also provided by the subject invention are kits and systems for practicing the subject methods, i.e., for using DBRs to determine the number (or minimum number), of different starting polynucleotides that have been sequenced for a particular polynucleotide. As such, systems and kits may include polynucleotides containing DBRs (e.g., adapters) as well as any other functional domains of interest as described herein (e.g., sequencing primer sites, MIDs, reflex sequences, etc.). Systems and kits may also include and regents for performing any steps in attaching adapters to polynucleotides in a parents sample, preparing a parent sample for adapter/DBR attachment, and/or reagents for performing sequencing reactions (e.g., ligases, restriction enzymes, nucleotides, polymerases, primers, sequencing primers, dNTPs, ddNTPs, exonucleases, etc.). The various components of the systems and kits may be present in separate containers or certain compatible components may be precombined into a single container, as desired.

The subject systems and kits may also include one or more other reagents for preparing or processing a nucleic acid sample according to the subject methods. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step according to the present invention.

In addition to above-mentioned components, the subject kits typically further include instructions for using the components of the kit to practice the subject methods, e.g., to employ DBR as described above. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control samples and reagents, e.g., two or more control samples for use in testing the kit.

EXAMPLES

Methods

Two identical samples of mouse genomic DNA were labeled with adapters. One sample used an adapter that has a redundantly synthesized region consisting of 7 bases (RYB-DHVB), each of which could be one of two (for R and Y positions) or three (for B, D, H or V positions) bases (or a total of 972 different sequences) followed by the bases AC$\underline{A}$; the second sample used an adapter that has a redundantly synthesized region consisting of 7 bases (RYBDHVB), each of which could be one of two (for R and Y positions) or three (for B, D, H or V positions) bases (or a total of 972 different sequences) followed by the bases AC$\underline{G}$. Note the bolded underlined bases correspond to a synthetic polymorphic site. In these adapters, the sequence RYB serves as the DBR region and the DHVB serves as the MID. Thus, there were 12 possible DBR (2×2×3) codes and 81 different MIDs present (3×3×3×3).

The two samples were then mixed together in equal amounts to create, in effect, a perfect 50/50 heterozygote of A and G three bases downstream from the MID (i.e., the DHV$\overline{\text{B}}$ sequence). Different amounts of the mixture (100 ng, 300 ng, 600 ng, 2500 ng, 5000 ng, and 10,000 ng) were subjected to hybridization pull-down reactions followed by amplification through 10 cycles of PCR with TiA and TiB primers. The capture probes employed were 5'-biotinylated 60-mer reverse phase cartridge purified oligonucleotides (BioSearch). After amplification with TiA and TiB, a secondary PCR reaction with TiA and a sequence-specific primer tailed with TiB (5'-CCTATCCCCTGTGTGCCTTGGCAGTCT-CAGGGACACCCAGCCAAGACAGC-3') (SEQ ID NO:1) was used to amplify a specific fragment. The PCR fragment generated from each sample in the hybridization pull-down/PCR was sent for 454 Ti Shot sequencing to determine the DBR, MID and A/G allele.

The amplicon sequence from the hybridization pull down/PCR is shown below (SEQ ID NO:2). The DBR region is underlined, the MID is in bold, and the allele (R, which corresponds to A or G) is bold underline.

CCATCTCATCCCTGCGTGTCTCCGACTCAG<u>RYB</u>DHVBAC<u>R</u>TAGAATGTGC

ATGGATCGTATGAGCACCTGTGGGCAGGGCAAGTGGCAGATGCCTTAGTG

GATCTCACTGGAAGCCTGGCAGAAAGGTGGAGCTTGAAGGATGTAACGAA

AGCCAGCGGCCAGCAGGACAGACCCAGTGGTGGGGAGCACAGAACTTGTC

GGCAGCTACTCCACCTGAAGGACCGGTGTCTAATCAGCTGCTCTGTGCTT

AGCCCCAGAGCAGGTACAGCTATGGCTACAACTCCCTCCACCATTAGCTT

GTTACAGAGAAGGAAATCGGTCCTTGAGAGGCTGTCTTGGCTGGGTGTCC

CTGAGACTGCCAAGGCACACAGGGGATAGG

Results

FIG. 1 shows the allele ratio for each MID in the sample. The numbers at the top of each of the 6 panels show the input mass of genomic DNA used (in nanograms). The abscissa shows, for any particular MID, the fraction of A sequencing reads, or calls, (i.e., the number of reads of one of the polymorphic bases at the synthetic SNP position) to the total number of calls, e.g., the ratio of (A calls)/(A calls+G calls). This is called the allele ratio. The ordinate is the number of MIDs observed with a particular allele ratio (the total number of MIDs, as noted above, is 81). Because the input DNA was known to be at a 50/50 A/G ratio, the allele ratio for each sample should be 0.5.

At low input mass, the allele ratio is distorted—either too high or two low—because the molecules on the input to the first PCR step were limiting and so one of the two alleles was preferentially observed. As mass into the first step increases, both alleles are observed and at closer and closer to the expected 0.5 ratio. This analysis shows that there was considerable allele drop out at 100 ngs, 300 ngs and 600 ngs, while little to no allele drop out occurred at the higher input levels.

Figure 2:
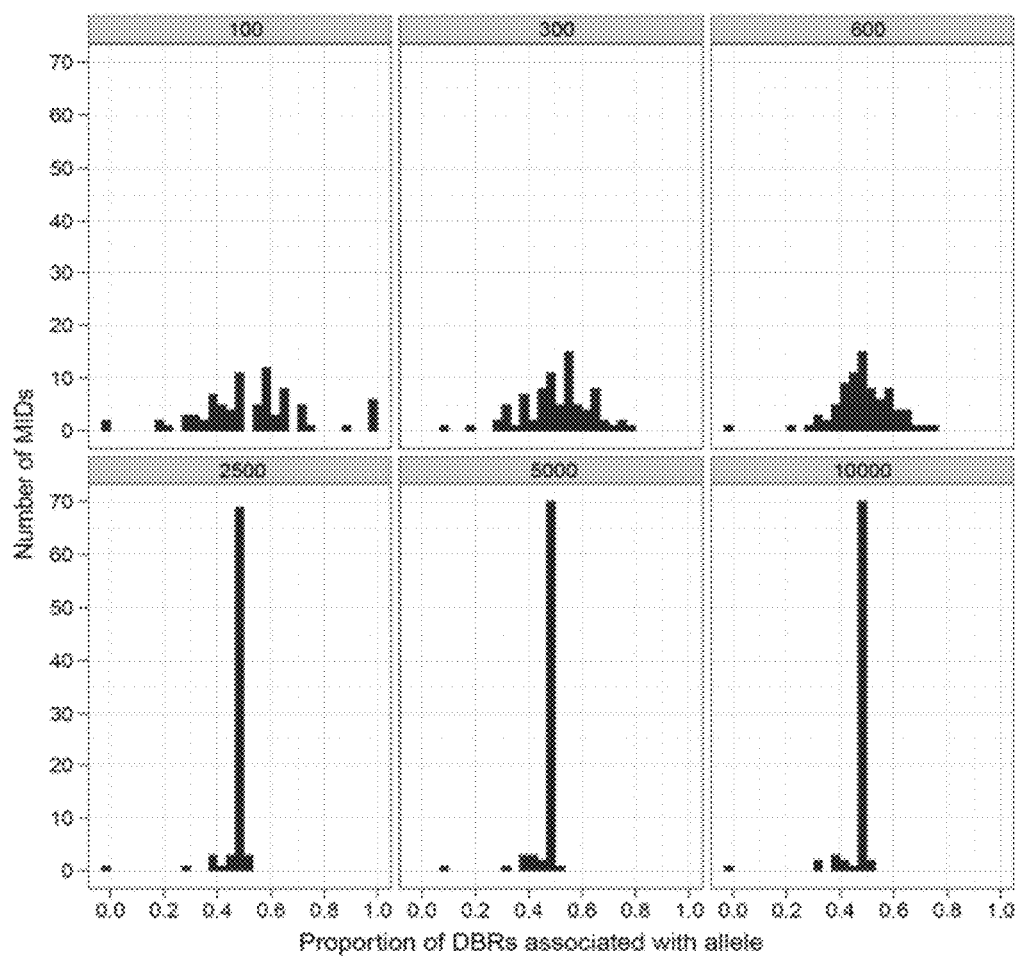
FIG. 2 shows the fraction of DBR sequences for each MID associated with each allele at a synthetic polymorphic position. Samples were prepared from the indicated amount of starting material (top of each panel; in nanograms).

FIG. 2 shows the fraction of DBR sequences for each MID associated with each allele. Since the input material is nominally 50/50 A and G at the synthetic polymorphic position, we would expect each of the 81 effective MIDs to be associated with 50% A reads and 50% G reads (as noted above). Furthermore, since the 12 DBRs are random and are associated with each of the 81 different MIDs, one would expect, with sufficient input DNA copies, that all 12 DBRs would be observed for the A allele and all 12 for the G allele. Thus, the fraction of DBRs observed for a particular base in the ideal case would be 12/24 or 0.5 for each allele. To the extent that insufficient numbers of molecules go into the processing steps, there may be less than 12 DBRs for each MID allele, and so the ratio can stray away from the ideal.

In FIG. 2, the abscissa shows, for any particular MID, the proportion of the DBRs actually observed for each allele divided by the total number of DBRs actually observed. The ordinate is the number of MIDs observed with a particular proportion or DBRs associated with an allele. There are, and should be, a total of 81 different MIDs seen. We observe that at low input mass, one frequently can see a distorted proportion—either too high or two low. This is likely due to limiting number of molecules input into the first PCR step, and so one of the two alleles was preferentially observed. As mass into the first step increases, both alleles are observed more frequently and associated with each allele is an observation of more and more of the DBRs, and thus a proportion closer to the 0.5.

A comparison of the date in FIGS. 1 and 2 shows an additional feature of employing DBRs as described herein. For a true heterozygote, one starts to see sooner (i.e., at lower mass) in the DBR analysis (FIG. 2) that the distribution clusters around the expected 0.5 ratio. This makes sense because, for example, observation of 6 of the 12 DBRs for the A allele and 4 of the 12 DBRs of the G allele would result in a proportion of (6/[6+4])=0.60 which, in fact is fairly close to the expected 0.5. The net effect is that the use of DBRs gives much greater confidence in the presence of a true heterozygote or true homozygote.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for enhancing a determination of the presence of alleles in a genomic sample, said method comprising:
   a) attaching a set of oligonucleotides that comprises a degenerate base region (DBR) comprising at least one nucleotide base selected from: R, Y, S, W, K, M, B, D, H, V, N and modified versions thereof to the nucleic acid molecules of a genomic sample that contains a polymorphic target region, thereby producing a population of adapter-attached polynucleotides in which each of said adaptor-attached polynucleotides that comprises said polymorphic target region is attached to a DBR sequence of an oligonucleotide of said set of oligonucleotides, wherein said oligonucleotides further comprise a unique multiplex identifier (MID) sequence that identifies a source for each of the nucleic acid molecules to which it is attached;
   b) amplifying the adapter-attached polynucleotides, thereby producing amplified adapter-attached polynucleotides that contain the polymorphic target region;
   c) sequencing some of the amplified adapter-attached polynucleotides that contain the polymorphic target region, thereby producing a plurality of sequences, wherein the sequencing step provides, for each of the amplified adaptor-attached polynucleotides that contain the polymorphic target region and are sequenced: (i) the nucleotide sequence of at least a portion of said polymorphic target region and (ii) the DBR sequence of the oligonucleotide to which said polymorphic target region is attached;
   d) determining, for one allele of the polymorphic target region, the number of different DBR sequences in the oligonucleotides that are associated with said allele; and
   e) repeating step d) for additional alleles of said polymorphic target region, thereby enhancing said determination of the presence of said alleles in said genomic sample based on the numbers of different DBR sequences in the oligonucleotides that are associated with said allele and said additional alleles.

2. The method of claim 1, further comprising:
   f) independently calculating the likelihood that each of the alleles is present in said genomic sample using the numbers of different DBR sequences in the oligonucleotides that are associated with said allele and said additional alleles; and
   g) calling a genotype for said genomic sample based on the likelihood calculated in step f).

3. The method of claim 1, wherein said oligonucleotides comprise a degenerate base region comprises at least 2 nucleotide bases, wherein each of the at least 2 nucleotide bases are selected from: R, Y, S, W, K, M, B, D, H, V, N, and modified versions thereof.

4. The method of claim 3, wherein the degenerate base region comprises from 3 to 20 nucleotide bases, wherein each of the 3 to 10 nucleotide bases is selected from: R, Y, S, W, K, M, B, D, H, V, N, and modified versions thereof.

5. The method of claim 1, wherein the oligonucleotides further comprises a sequencing primer site.

6. The method of claim 1, wherein said method further comprises combining said population of adapter-attached polynucleotides with other populations of adaptor attached polynucleotides, and wherein each of said populations of adaptor attached polynucleotides is associated with said unique MID sequence.

7. The method of claim 1, wherein said sequencing step comprises sequencing said some of the amplified adapter-attached polynucleotides on a next-generation sequencing platform.

8. The method of claim 1, wherein the genomic sample containing said polymorphic target region is enriched prior to the attaching step.

9. The method of claim 1, wherein the genomic sample containing said polymorphic target region is enriched prior to the sequencing step.

10. The method of claim 1, wherein the genomic sample comprises polynucleotides made from a tumor tissue.

11. The method of claim 1, wherein the genomic sample comprises polynucleotides made from microorganisms and/or viruses.

12. The method of claim 1, wherein said attaching step comprises ligating said set of oligonucleotides to the nucleic acid molecules of said genomic sample.

13. The method of claim 1, wherein said set of oligonucleotides are primers and the attaching step is done by primer extension.

14. The method of claim 1, wherein said genomic sample comprises multiple genomic samples derived from different sources.

15. The method of claim 14, wherein each of the multiple genomic samples is derived from a different subject.

16. The method of claim 14, wherein each of the multiple genomic samples is derived from a different human subject.

17. The method of claim 14, wherein the multiple genomic samples are derived from different sections of a tumor.

18. The method of claim 14, wherein the multiple genomic samples are derived from different tumors from a subject.

19. The method of claim 14, wherein the multiple genomic samples are derived from a subject over time.

20. The method of claim 19, wherein the polymorphic target region is in a viral sample.

* * * * *

UNITED STATES PATENT AND TRADEMARK OFFICE
CERTIFICATE OF CORRECTION

PATENT NO. : 8,481,292 B2  
APPLICATION NO. : 13/237124  
DATED : July 9, 2013  
INVENTOR(S) : James Casbon Page 1 of 1

It is certified that error appears in the above-identified patent and that said Letters Patent is hereby corrected as shown below:

On the Title page of the patent, under Item (73), listing the Assignee, delete "Population Genetics Technologies Litd.," and insert --Population Genetics Technologies Ltd.,--.

Signed and Sealed this  
Twenty-third Day of December, 2014

Michelle K. Lee  
*Deputy Director of the United States Patent and Trademark Office*